United States Patent
Nichtl

(10) Patent No.: US 6,833,275 B1
(45) Date of Patent: Dec. 21, 2004

(54) GOLD CONJUGATES CONTAINING DETERGENT

(75) Inventor: Alfons Nichtl, Hohenpeissenberg (DE)

(73) Assignee: Roche Diagnostics GmbH (DE)

(*) Notice: Subject to any disclaimer, the term of this patent is extended or adjusted under 35 U.S.C. 154(b) by 0 days.

(21) Appl. No.: 09/633,295

(22) Filed: Aug. 7, 2000

Related U.S. Application Data

(62) Division of application No. 09/120,230, filed on Jul. 22, 1998, now abandoned.

(30) Foreign Application Priority Data

Jul. 22, 1997 (DE) .......................... 197 31 469

(51) Int. Cl.$^7$ ............................. G01N 33/544
(52) U.S. Cl. .................. 436/528; 436/523; 436/524; 436/525; 436/73; 436/80; 436/323; 156/279; 205/169; 427/189; 427/191; 427/196; 427/201; 427/205; 424/278.1; 252/180.25; 252/182.29; 252/183.19
(58) Field of Search .................... 436/528, 523, 436/524, 525, 73, 80, 823; 156/279; 205/109; 427/189, 191, 196, 201, 203; 424/278.1; 252/186.25, 182.29, 183.19

(56) References Cited

U.S. PATENT DOCUMENTS

| | | | | |
|---|---|---|---|---|
| 4,014,808 A | * | 3/1977 | Herpers, Jr. et al. | 252/135 |
| 4,018,720 A | * | 4/1977 | Lengyel et al. | 252/534 |
| 4,468,339 A | * | 8/1984 | Rysek et al. | 252/75 |
| 4,622,362 A | * | 11/1986 | Rembaum | 525/54.1 |
| 4,853,335 A | * | 8/1989 | Olsen et al. | 436/527 |
| 5,102,788 A | * | 4/1992 | Cole | 435/7.9 |
| 5,120,643 A | * | 6/1992 | Ching et al. | 435/7.92 |
| 5,141,850 A | | 8/1992 | Cole et al. | 436/525 |
| 5,200,270 A | * | 4/1993 | Ishida et al. | 428/403 |
| 5,225,460 A | * | 7/1993 | Sampath et al. | 523/409 |
| 5,376,556 A | * | 12/1994 | Tarcha et al. | 436/525 |
| 5,393,658 A | * | 2/1995 | Olsen | 435/7.26 |
| 5,514,602 A | * | 5/1996 | Brooks, Jr. et al. | 436/525 |
| 5,527,672 A | * | 6/1996 | Mansfield et al. | 435/6 |
| 5,571,726 A | * | 11/1996 | Brooks, Jr. et al. | 436/525 |
| 5,571,728 A | * | 11/1996 | Kraus | 436/534 |
| 5,597,531 A | * | 1/1997 | Liberti et al. | 423/57 |
| 5,681,755 A | * | 10/1997 | Noppe et al. | 436/525 |
| 5,736,413 A | * | 4/1998 | Uzan et al. | 436/526 |
| 5,783,455 A | * | 7/1998 | Wiegand et al. | 436/525 |
| 5,817,525 A | * | 10/1998 | deAlwis | 436/523 |
| 5,849,941 A | * | 12/1998 | Rosenberg et al. | 554/227 |
| 5,851,777 A | * | 12/1998 | Hunter et al. | 435/7.1 |
| 5,869,103 A | * | 2/1999 | Yeh et al. | 424/501 |
| 5,872,013 A | * | 2/1999 | Leunissen et al. | 436/525 |
| 5,910,554 A | * | 6/1999 | Kempe et al. | 536/320 |
| 5,925,573 A | * | 7/1999 | Colin et al. | 436/525 |
| 5,932,212 A | * | 8/1999 | Khalaf | 424/94.6 |
| 5,958,790 A | * | 9/1999 | Cerny | 436/501 |
| 5,972,720 A | * | 10/1999 | Nichtl et al. | 436/525 |

FOREIGN PATENT DOCUMENTS

| | | |
|---|---|---|
| EP | 0 311 094 | 4/1989 |
| EP | 0 489 465 | 6/1992 |
| WO | 90/13637 | 1/1990 |

OTHER PUBLICATIONS

Behnke et al., Non-specific binding of protein-stabilized gold sols as a source of error in immunocytochemistry, Eur. J. Cell. Biol. Bd. 41, Nr. 4, 1986, pp. 326–328.

* cited by examiner

Primary Examiner—Christopher L. Chin
Assistant Examiner—Pensee T. Do
(74) Attorney, Agent, or Firm—Rothwell, Figg, Ernst & Manbeck

(57) ABSTRACT

A composition which contains stabilized conjugates composed of colloidal particles and biomolecules is obtained by adding a detergent to a solution containing biomolecules before or/and during treatment of colloidal particles with this solution.

12 Claims, No Drawings

GOLD CONJUGATES CONTAINING DETERGENT

This application is a divisional application filed under 37 CRF § 1.53(b) of parent application Ser. No. 09/120,230, filed Jul. 22, 1998 now abandoned.

The invention concerns compositions which comprise colloidal particles on the surface of which biomolecules are adsorbed.

Conjugates of biomolecules, such as proteins or nucleic acids, and colloidal particles are widely used for example as signal transmitters or/and as capture reagents in diagnostic and therapeutic methods. They serve for example as markers in detection procedures such as immunoassays or as micro-projectiles for gene transfer. Particles that can be used are particles of metals and metal compounds such as metal oxides, metal hydroxides, metal salts and polymer cores which are coated with metals or metal compounds (cf. e.g. U.S. Pat. No. 4,313,734; Leuvering et al., J. Immunoassay 1 (1980), 77–91; Leuvering Dissertation (1984), Sol Particle Immunoassay (SPIA): The use of Antibody Coated Particles as Labelled Antibodies in Various Types of Immunoassay; Uda et al., Anal. Biochem. 218 (1994), 259–264, DE-OS 41 32 133, page 3, lines 16–18 for applications as a marker and Tang et al., Nature 356 (1992), 152–154; Eisenbraun et al., DNA and Cell Biology 12 (1993), 791–797; Williams et al., Proc. Natl. Acad. Sci. USA 88 (1991), 2726–2730 for gene transfer applications). Furthermore it is also known that non-metallic colloidal particles such as carbon particles can be used (van Amerongen, Anabiotic '92 (1993), 193–199). At present colloidal gold particles are most frequently used.

Biomolecule-gold conjugates are prepared by firstly preparing gold sols by generally known procedures by reducing tetrachloroauric acid. Subsequently the gold sols are loaded with the biomolecule desired in each case e.g. proteins such as antibodies, protein A, protein G, streptavidin etc. The respective loading conditions (pH, buffer, concentration of the biomolecules etc) depend on the isoelectric point of the biomolecules, the MPA (minimal protecting amount) or/and the specific application of the conjugate (cf. e.g. De Mey, The Preparation and Use of Gold Probes, in: Immunocytochemistry, publisher: J. M. Polak and S.V. Noorden, pages 115–145, Wright, Bristol 1986; J. E. Beesley, Colloidal Gold: A New Perspective for Cytochemical Marking, Microscopy Handbooks 17, Oxford University Press, 1989, in particular pages 1–14; G. Frens, Nature Physical Science, 241 (1973) 20–22; J. Roth, The Colloidal Gold Marker System for Light and Electron Microscopic Cytochemistry in: Immunocyto-chemistry 2 (1983 218–284)). Explicit reference is made to the disclosure of these documents.

After loading the colloidal particles with the respectively desired biomolecule, it is necessary to stabilize the conjugates. This stabilization is intended to reduce aggregation of the particles and to saturate remaining free surfaces that are accessible to adsorption. Stabilizers used in the state of the art are inert proteins e.g. bovine serum albumin, blood substitute mixtures etc., water-soluble technical polymers such as polyethylene glycol (molecular weight 20,000 D), polyvinylpyrrolidone, polyvinylalcohol, polyvinylsulfate, dextran and gelatin (cf. e.g. De Mey, Supra; Beesley, Supra; Behnke, Eur. J. Cell Biol. 41 (1986), 326–338; DE 24 20 531 C3; and Meisel et al., J. Phys. Chem. 85 (1981), 179–187). In addition the possibility of stabilizing gold sols by phosphane complex ligands has also been described (Schmid et al., Z. Naturforsch. 45b (1994), 989–994).

When loading colloidal gold particles the procedure is usually to adjust the solution of the protein to be adsorbed to the gold as well as the gold sol to a pH close to the isoelectric point (IP) of the protein. In this connection it has been regarded as essential in the state of the art for a successful loading that the protein solution should if possible contain no additives and e.g. the ionic strength should not be above 10 mM. For the loading the protein solution is added to the gold sol while stirring or vice versa. After the protein has bound to the gold particles, a solution of a suitable stabilizer is added. Optionally the conjugate formed is subsequently purified e.g. by ultra-centrifugation or gel filtration.

The stabilizers used according to the state of the art bind adsorptively to the free surfaces of the metal particles. Longer storage or changes in the ambient conditions such as those which occur in a test by contact with the sample (blood, serum, plasma, urine), incorporation of the conjugates in test strip fleeces etc., can desorb or displace the stabilizers from the surfaces to a greater of lesser extent. This leads to a deterioration of the aggregation stability and to an increase in the unspecific reactivity. Moreover most of the stabilizers used are poorly defined products with variable quality in some cases e.g. bovine serum albumin, gelatin. This can also cause variations in the stabilizing effect.

Adsorption processes on particle surfaces are very complex and hitherto are only partially understood. It is assumed that the adsorption is due to a combination of electrostatic interactions, Van-der Waals forces and hydrophobic interactions (Beesley, Supra). Depending on the type of adsorbed biomolecule, the one or the other type of binding can dominate in this process.

Aggregates form to a certain extent in the protein-gold conjugates according to known techniques. These undesired aggregates frequently already occur before addition of the stabilizer. The reasons for the formation of aggregates can for example be that "sticky" proteins i.e. proteins with a hydrophobic surface bind together and consequently also bridge the gold particles to which they are conjugated. Therefore it has for example been described that IgG preparations should be freed of aggregates by ultracentrifugation before coupling to gold (W. D. Geoghegan, G. A. Ackerman, J. Histochem. Cytochem. 25 (1977), 1187–1200). Furthermore it is possible that hydrophobic patches that are not covered by protein on the surface of noble medal particles and in particular gold particles can interact with one another and form particle aggregates. A further cause for the occurrence of undesired aggregates can also be that hydrophobic patches on the noble metal surface that are not covered by protein interact with hydrophobic patches on proteins conjugated to neighbouring gold particles and thus cross-link the gold particles.

One frequently also observes a secondary cross-linking of protein gold conjugates which also occurs when the conjugates have already been saturated with a stabilizer. This is probably due to the fact that even after the action of conventional stabilizers, hydrophobic patches remain on the gold surface or/and on the conjugated protein by means of which an uncontrolled aggregation of protein-gold particles occurs with slow kinetics. These problems do not only occur in conjugates containing particles of gold but also in particles made of other solids, especially other metals.

Therefore the object of the present invention was to provide conjugates of colloidal particles and biomolecules in a stable form which do not have the disadvantages of the state of the art.

Surprisingly it has been found that detergents are extremely suitable for stabilizing biomolecule particle conjugates. One subject matter of the invention is therefore a composition which comprises colloidal particles on the surface of which biomolecules are adsorbed wherein the composition additionally contains a detergent.

It was found that the addition of detergents to colloidal particles, for example to a gold sol, before loading with biomolecules and/or to a solution containing biomolecules before and/or during loading of the colloidal particles, impairs binding to the particles to an extent that is considerably less than would have been expected by a person skilled in the art, and is surprisingly advantageous in several respects. The addition of detergent according to the invention prevents aggregation processes that already take place with conventional stabilizers before conjugation and before re-loading and this improves the reproducibility of the manufacturing process for the conjugates and leads to a more uniform size distribution of the conjugates i.e. an increased monodispersity.

A substantial improvement in the stability of the conjugates is achieved compared to the stabilizers of the state of the art. In particular the slow after-aggregation of already stabilized biomolecule particle conjugates which occurs with conventional compositions is suppressed. This leads to an improved long-term stability and a lower aggregation tendency in solution, to an improved stability against changes in the ambient conditions and to an improved test function e.g. improved chromatographic properties. The addition of detergent considerably improves the function of biomolecule-particle conjugates and in particular the function of biomolecule-gold conjugates in tests. Hence for example the non-specific binding which corresponds to the blank reading in the test is reduced.

It was particularly surprising that the improvements could be achieved without adversely influencing the function of the conjugates for example by displacing the biomolecules by the detergent or by possible interactions of the biomolecules or the colloidal particles with the detergent.

The composition according to the invention can be present as an aqueous suspension and also immobilized for example on a chromatographic material such as an absorbent paper.

The particles can be metallic or non-metallic particles such as carbon particles. Metallic particles are preferred such as particles of metals, metal oxides, metal hydroxides, metal compounds or particles coated with metals or metal compounds. Metal particles are particularly preferred.

The metal particles are preferably noble metal particles e.g. metals selected from the group comprising gold, silver, copper, platinum, palladium and mixtures thereof. Gold particles are particularly preferred.

The mean diameter of the particles is—as usual in the state of the art—in the range of 1 to 1000 nm and can be varied according to the application purpose. The mean diameter of the particles is preferably in the range of 2 to 200 nm and especially preferably 2 to 100 nm.

The biomolecules adsorbed to the surface of the particles are preferably selected from the group comprising proteins, glycoproteins, peptides, nucleic acids, peptidic nucleic acids, saccharides, antigens and haptens. Biomolecules are particularly preferably selected from the group comprising antibodies, antibody fragments, lectins, enzymes, streptavidin, avidin, protein A, antigens, such as recombinant polypeptides or multiple antigens (cf. WO96/03652), e.g. polyhaptens (several haptens or peptides coupled to a carrier such as dextran or to a protein), peptides and haptens (low molecular substances preferably with a MW $\leq 1500$ such as biotin, fluorescein or digoxigenin). With regard to the exact conditions for adsorption of these biomolecules to gold particles, reference is made to the already mentioned review article of De Mey and Beesley.

According to the invention detergents that can be used are anionic, cationic, ampholytic or non-ionic surface-active substances, in particular surfactants. The compositions according to the invention preferably contain an ethoxylate detergent and particularly preferably polyethoxysorbitan laurate and/or oleate or/and laurylpolyethylene glycol ether as a detergent. These detergents are commercially available under the brand names TWEEN® and Brij® (e.g. TWEEN 80, TWEEN 20, Brij 35).

The detergent is preferably used at a concentration which does not exceed the critical micelle concentration. In this connection the critical micelle concentration is understood as that concentration at which higher aggregates, so-called micelles, are formed from the surfactant molecules. Attainment of the critical micelle concentration can be easily determined by the jump in physical properties such as for example the surface tension, the osmotic pressure, the equivalent conductivity, the interfacial tension and/or the density. Each of these parameters can be measured with known methods.

The optimal detergent concentration depends on the respective properties of the biomolecule to be conjugated and it must be individually determined for each biomolecule. The optimal detergent concentration is present when, on the one hand, an adequate amount of biomolecules bind to the surface of the colloidal particles and, on the other hand, unspecific hydrophobic interactions are substantially suppressed. The detergent is preferably present at a concentration of 0.0001 to 1 mM, particularly preferably 0.001 to 0.1 mM (final concentration in the conjugation preparation).

The composition according to the invention can be prepared by adding a detergent to colloidal particles before loading with biomolecules or/and to a solution containing biomolecules before or/and during loading of the colloidal particles with this solution.

The compositions according to the invention can be used as a detection reagent, in particular as an immunological detection reagent. In a first preferred embodiment the detection reagent is used in an immunoassay i.e. in a method for the determination of an analyte in a sample liquid by means of immunological methods e.g. by a competitive assay in which a labelled analyte analogue or a labelled analyte-specific receptor e.g. an antibody is used, or a sandwich assay in which a labelled analyte-specific receptor or a labelled additional receptor that is capable of binding to the analyte-specific receptor is used. Preferred examples are pregnancy tests e.g. tests for the detection of human chorionic gonadotrophin (HCG) or methods for the detection of drugs such as cocaine or amphetamines, human serum albumin, troponin T, myoglobin and immunoglobulins such as anti-HIV antibodies. Particularly preferred forms of application are rapid tests in which the sample to be determined is applied to an absorbent material containing the detection reagent e.g. a test strip. A second particularly preferred embodiment in which the stabilized composition according to the invention can be used is the staining of tissue sections.

Furthermore the compositions according to the invention can of course also be used for all further applications that are known for biomolecule particle conjugates e.g. for gene transfer.

Yet a further subject matter of the present invention is a process for stabilizing conjugates of colloidal particles and biomolecules in which a detergent is added to colloidal particles, in particular gold sol, before loading and/or to a solution containing biomolecules before or/and during the loading of the colloidal particles with this solution. In this manner it is possible to achieve an increased long-term stability of the conjugates as well as an improved pH stability and an improved stability against the presence of other substances. In these applications the detergent is preferably used in an amount at which the micelle concentration is not exceeded. The detergent is preferably used in an amount which results in a final concentration of 0.0001 to 1 mM, preferably 0.001 to 0.1 mM.

Furthermore after the loading one can also use additional stabilizers known from the state of the art such as inert proteins e.g. bovine albumin or/and polyethylene glycols.

Finally the present invention also concerns a test kit for an immunological method of detection which contains a composition stabilized according to the invention as a detection reagent.

The invention is further elucidated by the following examples.

EXAMPLE 1 (COMPARATIVE EXAMPLE)

Preparation of protein-gold conjugates

A solution of the protein to be adsorbed to gold particles was dialysed against a suitable loading buffer or diluted with a loading buffer. Subsequently aggregates that may have formed were removed by centrifugation or filtration through a 0.2 $\mu$m filter.

The pH of the solution containing the colloidal gold particles was adjusted with $K_2CO_3$ to the pH of the protein solution. Then the colloidal gold solution was added while stirring to the protein solution. The volume ratio of protein solution to colloidal gold solution was 1:10 in this case.

The protein-gold conjugates prepared in this manner were stabilized according to the state of the art by addition of a BSA solution up to a final concentration of 0.01% to 3% (w/v) or by addition of a polyethylene glycol solution up to a final concentration of 0.01% to 0.1% (w/v).

subsequently the protein-gold conjugates were purified and concentrated and the desired storage buffer conditions were set e.g. 20 mM Tris, 100 mM NaCl pH 8, 1% BSA or/and 0.01% to 0.1% PEG, $NaN_3$.

EXAMPLE 2

Influence of the time of the detergent addition during the conjugation of PAS <digoxin>S-IgG (IS) (explanation: polyclonal anti-digoxin antibody from sheep, immunosorbed IgG preparation) to 20 nm gold sol.

The hydrophobic antibody PAB <digoxin>S-IgG (IS) was conjugated to a gold sol with a particle diameter of 20 nm. The conjugation was carried out in a solution with a pH of 8.5. Starting with a gold sol referred to as M843, a protein-gold conjugate was formed with addition of the hydrophobic antibody at a final concentration of 5 $\mu$g/ml. In this connection the experimental preparation 2a represents a conjugate prepared according to the state of the art without detergent addition. 0.04 mM Brij 35 was added at different times to the experimental preparations 2b to 2e. The respective ratios of OD at 550 nm and at 600 nm are given in Table 1. This value is a parameter for the uniformity of the size distributions. The lower this value, the higher is the proportion of aggregates and the more inhomogeneous is the size distribution of the conjugate particles. Correspondingly it is desirable to have an OD 550/600 value which is as high as possible. Table 1 additionally shows the mean diameter of the conjugate particles measured with photon correlation spectroscopy named PCS. The diameter of the conjugate particles and thus the value of PCS should be as low as possible.

The procedure was generally that firstly the unloaded initial gold sol was mixed with the IgG to form the biomolecule-gold conjugate. After addition of the IgG solution to the gold sol, the conjugate was reloaded with BSA (bovine serum albumin) as a stabilizer. In the experimental preparation 2b the detergent was added to the gold solution before. addition of the IgG (the IgG solution was diluted 1:10 when added to the gold sol); in the experimental preparation 2c the detergent was added to the IgG solution; in experimental preparation 2d the detergent was added immediately after addition of the IgG solution to the gold sol but before reloading with BSA and in experimental preparation 2e the detergent was added after retreatment with BSA had been completed.

TABLE 1

PAB < digoxin > S-IgG (IS; 07) gold conjugates

| experimental preparation | IgG conc. [$\mu$g/ml] | OD 550/600 | PCS [nm] | remarks |
|---|---|---|---|---|
| M843 | — | 3.94 | 21.5 ± 3.7 | GOLD SOL |
| 2a | 5 | 3.87 | 107 ± 42 | (comparative example) |
| 2b | 5 | 4.08 | 65 ± 33 | =2a, but additionally 0.04 mM Brij 35 before IgG |
| 2c | 5 | 4.06 | 58 ± 30 | =2a, but additionally 0.4 mM Brij 35 in IgG solution |
| 2d | 5 | 3.9 | 100 ± 46 | =2a, but additionally 0.04 mM Brij 35 after IgG |
| 2e | 5 | 3.8 | 94 ± 46 | =2a, but additionally 0.04 mM Brij 35 after BSA |

As can be seen from Table 1, the experimental preparations 2b and 2c have the most favourable properties. The conjugates obtained have, incomparison to the state of the art, a considerably improved diameter and a high OD 550/600 value i.e. a relatively uniform size distribution of the particles. Hence the PAB-PAB, gold-gold and unspecific PAB-gold interactions based on hydrophobic forces are suppressed best by the addition of a detergent before or/and during the loading of the gold sol.

EXAMPLE 3

Influence of the time of detergent addition in the conjugation of recombinant HIV antigen p24 to 40 nm gold sol Gold sol with an average particle size of 40 nm (M 825) was loaded with the recombinant HIV antigen p24 at a concentration of 5 μg/ml. The pH of the solutions was in each case adjusted to 8.0. The procedure was similar to that described in example 2. p24-gold conjugates were formed by addition of the antigen p24 to the gold sol. Subsequently a reloading was carried out by adding BSA as a stabilizer. In the experimental preparation 3b 0.04 mM Brij 35 was additionally added to the gold sol before the p24 addition; in experimental preparation 3c 0.4 mM Brij 35 was added to the p24 solution (the p24 solution was diluted 1:10 in the subsequent addition to the gold sol) and in experimental preparation 3d 0.04 Brij 35 was added after reloading with BSA had been completed.

EXAMPLE 4

Addition of various detergent concentrations in the conjugation of NAB <PSA>M-10-IgG (murine monoclonal anti-PSA antibody No. 10, IgG preparation) to 20 nm gold sol.

MAB<PSA>M-10-IgG gold conjugates were formed by addition of MAB<PSA>M-10-IgG to 20 nm gold sol. The detergent was added in the stated concentrations to the MAB<PSA>M-10-IgG solution. The results are shown in Table. 3.

For the MAB<PSA >M-10-IgG a final Brij concentration of 0.005 to 0.01 mM was determined as optimal. Overall it was found that a higher detergent concentration is required for more hydrophobic proteins than for less hydrophobic proteins.

TABLE 3

MAB < PSA > M-10-IgG gold
(from 20 nm gold sol)
Optimization of the Brij 35 concentration in the loading mixture

| Experimental preparation | IgG added μg/ml | Brij 35 mM | IgG in the supernatant (% of IgG added) | OD 550/600 | Diameter acc. to PCS nm | remarks |
|---|---|---|---|---|---|---|
| 4a | 2 | 0 | 0.1 | 2.60 | 57 | state of the art, not suitable in test strips |
| 4b | 2 | 0.005 | 3 | 3.53 | 32 | suitable in test strips |
| 4c | 2 | 0.01 | 6 | 3.57 | 30 | suitable in test strips |
| 4d | 4 | 0.005 | 9 | 3.42 | 30 | suitable in test strips |

TABLE 2 p24 (02)-gold conjugates

| experimental preparation | remarks | yield [%] | OD 550/600 | PCS [nm] |
|---|---|---|---|---|
| M 825 | gold sol | 100 | 2.41 | 43 ± 24 |
| 3a | (comparative example) | 78 | 2.06 | 83 ± 45 |
| 3b | =3a but additionally 0.04 mM Brij 35 before p24 addition | 93 | 2.12 | 63 ± 36 |
| 3c | =3a but additionally 0.4 mM Brij 35 in p24 solution | 92 | 2.13 | 63 ± 35 |
| 3d | =3a but additionally 0.04 mM Brij 35 after BSA addition | 85 | 2.01 | 67 ± 24 |

Also in this case a considerable improvement of the parameters OD 550/600 as well as PCS can be seen in comparison to experimental preparation 3a without the addition of Brij 35.

EXAMPLE 5

Stability of the Conjugates

The stability of gold conjugates prepared according to the invention was examined in comparison to conventionally prepared gold conjugates. Starting with the same MAB<HCG>-IgG and 40 nm gold sol in each case a MAB<HCG>IgG-gold conjugate was prepared by the same procedure in two preparations. In preparation 5a the preparation was carried out by adding the protein solution to the gold sol without the addition of detergent, in preparation B the IgG solution used to load the gold sol contained 0.1 mM Brij 35. The characteristic parameters OD 550/660 and the diameter PCS were in each case examined immediately after preparation of the conjugate i.e. after addition of BSA as a stabilizer as well as after storage at 4° C. at regular intervals up to 27 weeks. In preparation 5a the particle size increased considerably during storage and the value for OD 550/600 decreased whereas in the preparation 5b according to the invention both parameters only changed slightly. This shows that the protein-gold conjugates according to the invention are considerably more stable than the protein-gold conjugates prepared according to the state of the art.

TABLE 4

MAB < HCG > -IgG-gold
(from 40 nm gold sol)
Examination of the stability of gold conjugates on long-term storage at +4° C.

| | Brij 35 | OD 550/600 | | diameter accord. to PCS (nm) | |
|---|---|---|---|---|---|
| Preparation | mM in IgG solution | immediately after preparation | after 27 weeks at +4° C. | immediately after preparation | after 27 weeks at +4° C. |
| 5A | 0 | 2.35 | 1.92 | 61 | 105 |
| 5B | 0.1 | 2.37 | 2.26 | 58 | 62 |

EXAMPLE 6

Use of Gold Conjugates in Troponin Test Strips

A series of conjugates composed of MAB<troponin T>M-11-7-IgG and 40 nm gold sol were compared with regard to their function in the Trop T test strip. The conjugates prepared in preparation 6a and preparations 6b to 6g differed mainly in that in preparation 6a loading was carried out without detergent, but in preparations 6b to 6g with 0.075 mM Brij 35 in the IgG solution.

As can be seen in the last column of table 5 non-specific blanks occur in the test strips with conventionally prepared gold conjugates which are so high that the conjugate cannot be used in this case. In contrast the conjugates according to the invention coated in the presence of Brij result in no blank or only a slight blank and are hence suitable for the test strips.

TABLE 5

MAB < TN-T > M-11-7-IgG-gold conjugates

| Preparation | size PCS [nm] | $OD_{550}/OD_{600}$ | TS evaluation (blank = unspec. binding/blank) | TS evaluation (cut off) | TS suitability |
|---|---|---|---|---|---|
| 6a | 54 | 2.26 | strong blank | cannot be determined | not ok due to the blank |
| 6b | 54 | 2.26 | slight blank (after 20 min) | 0.05 ng/ml | ok |
| 6c | 50 | 2.17 | hardly blank (after 20 min) | 0.05 ng/ml | ok |
| 6d | 57 | 2.31 | slight blank (after 30 min) | 0.05 ng/ml | ok |
| 6e | 51 | 2.11 | slight blank (after 30 min) | 0.05 ng/ml | ok |
| 6f | 56 | 2.31 | no blank | 0.05 ng/ml | ok |
| 6g | 52 | 2.27 | no blank | 0.05 ng/ml | ok |

What is claimed is:

1. A method for stabilizing the biomolecule function of conjugates composed of colloidal particles and biomolecules, the method comprising:
   a) adding an amount of detergent that does not exceed a critical micelle concentration, wherein the concentration of said detergent is 0.001 to 1 mM, to a solution containing biomolecules, and
   b) thereafter loading particles in a colloidal state with said solution of biomolecules to form conjugated colloidal particles, wherein said detergent does not adversely influence the biomolecules or the conjugated particle function of said conjugated colloidal particles by displacing the biomolecules from said conjugated colloidal particles.

2. The method of claim 1, further comprising:
   adding an additional stabilizer after loading the colloidal particles.

3. The method of claim 2, wherein the additional stabilizer is an inert protein, polyethylene glycol, or a mixture thereof.

4. The method of claim 1, wherein the colloidal particles are selected from the group consisting of gold, silver, copper, platinum, palladium and mixtures thereof.

5. The method of claim 1, wherein the biomolecules are selected from the group consisting of antibodies, antibody fragments, lectins, enzymes, streptavidin, avidin, protein A, antigens, peptides and haptens.

6. A process for producing colloidal particles having biomolecule adsorbing surfaces, the process comprising:
   a) adding an amount of detergent that does not exceed a critical micelle concentration, wherein the concentration of said detergent is 0.001 to 1 mM, to a solution containing biomolecules, and
   b) thereafter contacting particles in a colloidal state with said solution of biomolecules to form conjugated colloidal particles, wherein said detergent does not adversely influence the biomolecule or the conjugated particle function of said conjugated colloidal particles by displacing the biomolecules from said conjugated colloidal particles.

7. The method of claim 6, wherein the colloidal particles are selected from the group consisting of gold, silver, copper, platinum, palladium and mixtures thereof.

8. The method of claim 6, wherein the biomolecules are selected from the group consisting of antibodies, antibody fragments, lectins, enzymes, streptavidin, avidin, protein A, antigens, peptides and haptens.

9. A method for stabilizing the biomolecule function of conjugates composed of colloidal particles and biomolecules, the method consisting essentially of:
   a) adding an amount of detergent that does not exceed a critical micelle concentration, wherein the concentration of said detergent is 0.001 to 1 mM, to a solution containing biomolecules,
   b) loading particles in a colloidal state with said solution of biomolecules to form conjugated colloidal particles, and
   c) thereafter adding an additional stabilizer, wherein said detergent does not adversely influence the biomolecule or the conjugated particle function of said conjugated colloidal particles by displacing the biomolecules from said conjugated colloidal particles.

10. The method of claim 9, wherein the additional stabilizer is an inert protein, polyethylene glycol, or a mixture thereof.

11. The method of claim 9, wherein the colloidal particles are selected from the group consisting of gold, silver, copper, platinum, palladium and mixtures thereof.

12. The method of claim 9, wherein the biomolecules are selected from the group consisting of antibodies, antibody fragments, lectins, enzymes, streptavidin, avidin, protein A, antigens, peptides, and haptens.

* * * * *